United States Patent [19]

Clark et al.

[11] Patent Number: 4,526,789

[45] Date of Patent: Jul. 2, 1985

[54] PROCESS FOR PREVENTING OR REVERSING CATARACT FORMATION

[75] Inventors: John I. Clark, Newton; Loretta S. Mengel; George B. Benedek, both of Belmont, all of Mass.

[73] Assignee: Massachusetts Institute of Technology, Cambridge, Mass.

[21] Appl. No.: 533,168

[22] Filed: Sep. 19, 1983

Related U.S. Application Data

[62] Division of Ser. No. 386,837, Sep. 6, 1982, Pat. No. 4,474,817.

[51] Int. Cl.$^3$ .............................................. A61K 31/11
[52] U.S. Cl. .................................. 514/627; 514/693; 514/694; 514/738
[58] Field of Search ........................................ 424/333

[56] References Cited

PUBLICATIONS

Chem. Abst. 93: 108038(c) (1980)–Clark et al.
Chem. Abst. 98: 104835(r) (1983)–Ting et al.
Chem. Abst. 99: 173918(c) (1983)–Jedziniak et al.

*Primary Examiner*—Douglas W. Robinson
*Attorney, Agent, or Firm*—Arthur A. Smith, Jr.; Paul J. Cook

[57] ABSTRACT

Cataract formation in mammalian lenses can be prevented or reversed by applying a solution of an aldehyde, an acrylamide or a glycol to the lens under conditions that permit the solution to interact with the lens constituents.

1 Claim, No Drawings 4,526,789

PROCESS FOR PREVENTING OR REVERSING CATARACT FORMATION

BACKGROUND OF TE INVENTION

The Government has rights in this invention under Grant No. 5 ROL EY00797-07 from the National Institute of Health.

This is a division of application Ser. No. 386,837 filed June 9,1982, now U.S. Pat. No. 4,474,817.

This invention relates to a process for preventing or reversing cataract formation in the lens of the eye.

Cataract disease is a worldwide medical problem causing blindness in over 1.25 million people annually. Cataracts generally are caused by structural inhomogeneities within lens tissue which become large enough to scatter light and reduce the normal transparency of the lens. The primary treatment for cataract is surgery and the surgical technique utilized comprises excising the cataract and, in some cases, replacing it with a plastic implant. This operation is delicate, expensive and is usually performed on elderly individuals which means that there may be significant risk to the patient. At the present time, there is no effective nonsurgical treatment for cataracts. It would be desirable to provide an effective nonsurgical treatment for cataracts either by way of prevention or reversal of the light scattering in order to avoid the inherent danger and expense associated with surgical techniques for removing cataracts.

SUMMARY OF THE INVENTION

The present invention is based on the discovery that certain classes of chemical reagents have the effect of inhibiting or reversing the formation of cataracts when administered to eye lenses. The reagents are glycols, aldehydes or acylamides and appear to interact with the protein constituents of the lens to prevent their association and to stabilize them against subsequent aggregation. An aqueous solution of the reagent which is physiologically acceptable to the eye is administered directly to the lens in a manner such that the solution penetrates the lens structure throughout its thickness for a period of time sufficient to permit interaction of the treating material with the protein substances in the lens. Depending upon the particular material utilized, stabilization of the protein in the lens against cataract formation or the reversal of cataract present in the lens can be reversible or irreversible.

DETAILED DESCRIPTION OF SPECIFIC EMBODIMENTS

In accordance with this invention, the lens of the eye is treated with a solution containing a chemical reagent which interacts with the protein molecules in the lens cytoplasm. The solution is applied to the lens for a period of time and under conditions such that the material which interacts with the protein molecules permeates the entire lens. The solution can be applied in any convenient manner such as with an eye dropper, microinjection, lysosomes, implanted timed release capsule or soaking apparatus. Generally, application of the treating composition is effected over a period of between about 6 and 16 hours but may be as short as 1 hour under normal room temperature condition. The chemical reagents utilized in the treatment prevent or reverse the aggregation of the protein molecules so as to eliminate light scattering and relieve the symptoms of cataract.

Depending on the chemical used in the treating solution, stabilization of the lens against cataract formation can be either reversible or irreversible. For example, when the treating solution contains an aldehyde, the aldehyde cannot subsequently be dialyzed out of the lens. It is believed that the aldehyde functions to covalently cross-link and/or extend the chain link of the portein molecules in the lens by interacting with the amino groups and/or other protonated moieties of the protein molecules. In contrast, when the treating material is a glycol or acrylamide, it can be dialyzed out of the lens subsequent to treatment in a reversible manner such that a lens which was rendered transparent by the initial treatment will revert to an opaque state upon removal of the glycol or acrylamide. However, if the acrylamide is covalently polymerized in-situ in the lens, by any conventional means, such as with a physiologically acceptable catalyst, the resultant polyacrylamide cannot be removed from the lens and the treatment of the lens becomes irreversible.

Representative suitable aldehydes are the dialdehydes and monoaldehydes which may be physiologically acceptable generally and to the eye specifically. Exemplary aldehydes include glutaraldehyde, acetaldehyde, formaldehyde, glyceraldehyde, glyoxal and acrolein or the like. Suitable acrylamides and glucols may also by physiologically acceptable to the eye. Exemplary acrylamides include acrylamide, methacrylamide or the like. In addition, it is to be understood that each of the reagents suitable for use herein may also be used in a mixture with one or more of any of the other suitable reagents.

The effective concentration and composition of the solution utilized in treatment will depend on the specific requirement that the solution be physiologically acceptable to the eye. Generally, the glycols are more innocuous than are the acrylamides or aldehydes and can be used in more concentrated solutions. The glycols are utilized in solutions of 1 to about 10 molar concentration. The aldehydes are utilized in solutions of 0.2 to 1.0 molar concentration and the acrylamides are utilized in solutions of 0.1 to 1.0 molar concentration. The carrier solutions are aqueous and can be buffered with a physiologically acceptable salt such as a phosphate in order to adjust the pH of the solution to approximately that of the lens and generally between about 7.35 to 7.45 pH units. In the case of acrylamides, a physiologically acceptable cross-linking catalysts such as riboflavin, hydrogen peroxide or radiation may be utilized to convert the arylamide to polyacrylamide thereby rendering the treatment irreversible. To test each compound, the lenses can be removed from the cataractous eyes and placed in solutions of the desired chemical. When so tested, it has been found that glycols will reverse opacification in hereditary cataracts in mice, in cataracts from galactosemic rats and diabetic rats, in human cataracts and in cataracts induce in calf lenses by low temperature or increased ionic strength. Unpolymerized acrylamide reverses cataracts induced to form in calf lenses. The induction of cataracts in calf lenses can be prevented when the transparent lenses are treated with aldehydes or with acrylamide that is then polymerized or cross-linked.

While the applicants do not intend to be limited to a specific theory regarding the mechanism of this invention, it is believed that the reagents in the present invention are involved in a chemical cross-linking of the protein molecules within the lens. The specific reagents that were tested as described below, increased the hardness of the lens, increased the amount of high molecular weight aggregate which could be extracted from the lenses and slowed the fluctuations in the intensity of scattered light from the lenses. These changes are characteristic of cross-linking reactions and furthermore the aldehydes are well known cross-linking reagents. An important control experiment was to inactivate the aldehydes with the amino acid, glycine, and then to treat the lens with the inactive compound. The inactivated aldehyde had no effect on lens opacification and no effect on the other properties related to cross-linking of the lens. It is likely that cross-linking in the lens is effected by the chemical modification of amino groups or other protonated moieties of the proteins in the cytoplasm of the lens cells. It is surprising that cross-linking would effect a reversal or prevention of opacification since cross-linking is generally regarded as a means for increasing the aggregated state of a protein solution. In this case, rather than causing aggregation of the cytoplasmic proptein molecules, cross-linking apparently stabilizes their molecular organization so that they cannot become aggregated to produce opacification.

It should be noted that the chemical mechanisms of aldehyde cross-linking may be quite different from acrylamide and glycol cross-linking. The aldehydes form covalent, intermolecular bonds between lens molecules, while acrylamide monomers polymerize to polyacrylamide which may include lens molcules in a copolymer. Both the aldehydes and acrylamide form covalent cross-links and are irreversible in their effects on opacification. In contrast, the glycols are easily diffused out of the lens. While the glycols have properties that are characteristic of cross-linking, they must act via weak non-covalent bonds. While the relationship between cross-linking and opacity is not fully explained, the test results suggest that opacification are inhibited by aldehydes, acrylamides and mild cross-linking agents, including glycols.

The following example illustrates the present invention and is not intended to limit the same.

EXAMPLE I

This example illustrates that glycols, aldehydes and acrylamides, including polyacrylamides can be utilized to improve the transparency of opacified eye lenses.

Solutions of 10% glycerol, 20% ethylene glycol, 4% glutaraldehyde, 1% acetaldehyde, 1% formaldehyde, and 5% acrylamide were made up in 0.15M phosphate-buffered saline of pH 7.2. Inactive solutions of 1% acetaldehyde and 1% glutaraldehyde were made up in phosphate-buffered saline by adding 3% glycine and they turned yellow within 10 minuted after being mixed. Lenses were placed in 50 ml of each solution for 16 hours and then correlation functions were determined and photographs were taken. The autocorrelation functions of the laser light scattered from the center of the lens were measured at 25° C. using a sampling time of 100 usec/channel. The auto-correlation function of the intensity fluctuation of scattered light from the lens is a measure of the size and mobility of scattering structures within the lens. See Benedek, Appl. Optics, 10, 459 (1971). A decrease in the mobility of the scattering element increases the decay time of the correlation function.

The nucleus of a calf lens opacifies when the temperature of the lens decreases below 17° C. When an opaque lens was soaked for 14 hours in 20% glycerol in 0.15M phosphate buffered saline, the normal transparency of the lens was maintained even at 5° C. When the lens was returned to 0.15M phophate buffered saline without glycerol and the glycerol diffused out of the lens, the nuclear opacity returned. This process was repeated several times in the same lens. Other glycols such as ethylene glycol and butanediol were shown to have the same effect by the same procedure. Although both the normal lens and the glycol-treated lens were transparent, their autocorrelation functions were quite different. The autocorrelation function for the normal lens decays rapidly and smoothly with $T\frac{1}{2} = 1300$ usec, while the autocorrelation function for the glycol-treated lens decays as much as 7 times slower than the normal lens. This change in the autocorrelation function from a fast to a slow decay has the characteristics of a concentrated protein solution or gel which has been stabilized by cross-linking. Other glycols such as 1,2 propanediol, 1,3 propanediol, 1,3 butanediol and 1,4 butanediol had the same clarifying effects as glycerol and ethylene glycol and their effects were reversible in the sense that after dialysing the glycol out of the lens, the opacity returned at 5° C.

Acetaldehyde, formaldehyde and glutaraldehyde cross-linked lenses were unable to opacify at 5° C. and the $T\frac{1}{2}$ of the autocorrelation function for aldehyde-treated lenses increased to as much as 13,000 usec. While the lenses were transparent, the aldehyde treatment produced a pale yellow color throughout the entire lens. It was not possible to dialyze the aldehyde out of the lenses as with glycerol and so nuclear opacification was not returned. When the aldehyde moiety was blocked by chemically reacting it with glycine and the lens then was blocked in the inactivated aldehyde, opacities still formed and the autocorrelation function was nearly the same as in the normal lens.

In other experiments, acrylamide was diffused into calf lenses and nuclear opacities could not be produced at 5° C. In the acrylamide-treated lens, the decay time of the auto-correlation function decreased as it did when aldehydes and glycols were diffused into lenses giving $t\frac{1}{2} = 4160$ usec. Like glycols, the acrylamide could be dialyzed out of the lens by returning it to 0.15M phosphate buffered saline, and the nuclear opacities could be formed again. However, when the acrylamide was diffused into a lens and then polymerized by the addition of persulphate and TEMED (tetramethylenediamine), the lens nucleus remained clear when the temperature was lowered to 5° C. Like aldehydes, the polyacrylamide could not be dialyzed out of the lens.

The results are summarized below in Table I.

TABLE I

|  | Transparency at 5° C. | Decay Time at 25° C. $T_{\frac{1}{2}}$ (usec) |
|---|---|---|
| Untreated Lens | opaque | 1300 |
| REVERSIBLE REAGENTS |  |  |
| 10% Glycerol | clear | 3920 |
| 20% Ethylene Glycol | clear | 9280 |
| IRREVERSIBLE REAGENTS |  |  |
| 2% Formaldehyde | clear | 12000 |
| 4% Glutaraldehyde | clear | 13000 |
| 2% Acetaldehyde | clear | 3040 |
| 2% Acetaldehyde + Glycine | opaque | 1500 |

TABLE I-continued

| | Transparency at 5° C. | Decay Time at 25° C. T½ (usec) |
|---|---|---|
| 5% Acrylamide | clear | 4160 |

We claim:

1. A process for preventing or reversing cataract formation in the lens of the eye which comprises administering topically to the eye an effective amount of a physiologically acceptable solution of a composition that interacts with constituents of the lens that cause lens opacification, said composition being an aldehyde selected from the group consisting of glutaraldehyde, acetaldehyde, formaldehyde, glyceraldehyde, glyoxal and acrolein and mixtures thereof.

* * * * *